United States Patent [19]

Kyotani et al.

[11] Patent Number: 5,204,251
[45] Date of Patent: Apr. 20, 1993

[54] PROCESS OF ENZYMATIC INTERESTERIFICATION MAINTAINING A WATER CONTENT OF 30-300 PPM USING RHIZOPUS

[75] Inventors: Susumu Kyotani; Isao Tsujimura; Hideki Fukuda, all of Takasago, Japan

[73] Assignee: Kanegafuchi Kagaku Kogyo & Kabushiki Kaisha, Osaka, Japan

[21] Appl. No.: 717,864

[22] Filed: Jun. 19, 1991

Related U.S. Application Data

[63] Continuation of Ser. No. 192,029, May 9, 1988, abandoned.

[30] Foreign Application Priority Data

May 11, 1987 [JP] Japan .................. 62-115475
Oct. 5, 1987 [JP] Japan .................. 62-250953

[51] Int. Cl.$^5$ .................. C12P 7/64; C12N 11/14
[52] U.S. Cl. .................. 435/134; 435/176; 435/939
[58] Field of Search .................. 435/134, 280, 176

[56] References Cited

U.S. PATENT DOCUMENTS

| | | | |
|---|---|---|---|
| 4,268,527 | 5/1981 | Matsuo et al. | 426/33 |
| 4,275,011 | 6/1981 | Tanaka et al. | 260/410 |
| 4,364,868 | 12/1982 | Hargreaves | 260/410 |
| 4,416,991 | 11/1983 | Matsuo et al. | 435/134 |

FOREIGN PATENT DOCUMENTS

| | | |
|---|---|---|
| 0064855 | 11/1982 | European Pat. Off. |
| 0079986 | 6/1983 | European Pat. Off. |
| 0126416 | 11/1984 | European Pat. Off. |
| 63-207393 | 8/1988 | Japan .................. 435/134 |
| 2035359 | 6/1980 | United Kingdom |
| 2042579A | 9/1980 | United Kingdom |
| 1577933 | 10/1980 | United Kingdom |
| 4119397A | 11/1983 | United Kingdom |
| 2147004A | 5/1985 | United Kingdom |

OTHER PUBLICATIONS

Zaks, A. et al., Proc. Natl. Acad. Sci. 82:3192-3196 (1985).

Primary Examiner—Douglas W. Robinson
Assistant Examiner—S. Saucier
Attorney, Agent, or Firm—Armstrong, Westerman, Hattori, McLeland & Naughton

[57] ABSTRACT

A process of an enzymatic interesterification in a low water content condition, which comprises subjecting a reaction liquid containing (a) a fat or oil and (b) a member selected from the group consisting of (i) another fat or oil, (ii) a fatty acid ester with a lower alcohol and (iii) a fatty acid to the action of a lipase in the form of dried Rhizopus cells while maintaining the water concentration between 5 and 1000 ppm in the reaction liquid during the reaction. In accordance with the process of the present invention, an interesterification of fat or oil can be carried out efficiently in a high yield.

1 Claim, 5 Drawing Sheets

PROCESS OF ENZYMATIC INTERESTERIFICATION MAINTAINING A WATER CONTENT OF 30-300 PPM USING RHIZOPUS

This application is a continuation of application Ser. No. 192,029 filed May 9, 1988, now abandoned.

BACKGROUND OF THE INVENTION

The present invention relates to a process of an enzymatic reaction in a low water content condition (a system containing a very small amount of water) wherein the reaction is carried out with adjusting the water concentration in the reaction system to a suitably very low value in order to effectively take advantage of the activity of enzyme and in order to suppress the formation of by-product, in an interesterification of a fat or oil for obtaining desired useful products by utilizing a enzymatic reaction.

As an use of technique of enzymatic reaction in a low water content condition, a production of substitutional fats for cacao butter known as a raw material of chocolates is exemplified. Further, by choosing kind of substrate and of lipase, various highly purified products having optional constitution of fatty acids can be produced.

In recent years, active studies on a process for preparing valuable a fat or oil by interesterification using lipase have been made.

The interesterification by lipase is generally considered to be caused by a reversible reaction of a hydrolysis in which triglyceride (TG) is hydrolyzed into diglyceride (DG), monoglyceride (MG) or glycerin and fatty acid (FA), and of synthesizing triglycerde again from the hydrolysates. Thus existence of water is necessary in an interesterification system, and therefore some amount of water is added to the reaction system.

However, it is impossible to inhibit the proceeding of the hydrolysis if the amount of water added is excess, and therefore by-products such as released fatty acid, monoglyceride and diglyceride are formed in a large amount and the yield of the desired triglyceride is lowered. And consequently, there arises a problem that the quality of triglyceride as the product is Therefore, in order to effectively carry out an interesterification, the reaction system should be maintained in a low water content condition constantly.

In case, however, the amount of water in a reaction system is too little, there arises a that the catalytic activity of enzyme cannot be sufficiently invigorated and the rate of reaction is lowered.

As a means of solving the above problem in the conventional process of interesterification, there is disclosed, for instance, an addition of a water-soluble polyhydroxy compound, and a protein or a peptide in an emulsion system (Japanese Unexamined Patent Publication No. 111398/1982), or an addition of a surface active agent (Japanese Unexamined Patent Publication No. 198798/1982) to increase the rate of reaction.

On the other hand, some processes for industrial production, in which an immobilized enzyme or a microorganism is used, have been proposed. For instance, a process in which an enzyme is immobilized onto an adsorbent such as Celite (Japanese Unexamined Patent Publication No. 71797/1980, Japanese Unexamined Patent Publication No. 104506/1977, Japanese Unexamined Patent Publication No. 84397/1980 and Japanese Unexamined Patent Publication No. 78496/1982); a process in which an enzyme is immobilized onto various water-absorptive materials such as saccharides (Japanese Unexamined Patent Publication No. 116688/1983, Japanese Unexamined Patent Publication No. 116689/1983, Japanese Unexamined Patent Publication No. 187195/1983 and Japanese Unexamined Patent Publication No. 28482/1984; a process in which a dried microbial cell is used as a catalyst (Japanese Unexamined Patent Publication No. 34189/1985); and the like are exemplified.

For industrially carrying out an interesterification using an immobilized enzyme or a microorganism, however, in both cases of batch reaction system and continuous reaction system, it is indispensable -to-. constantly adjust the water concentration in the vicinity of the enzyme to a suitably very low concentration in order to maintain a high yield. In an interesterification, since water is consumed by a hydrolysis, it is necessary to supply water properly. For instance, a process in which the reaction is proceeded with supplying a reaction liquid in which water is dissolved in an amount of 40 to 70% by weight of the saturated amount is disclosed (Japanese Unexamined Patent Publication No. 154951/1981 and Japanese Unexamined Patent Publication No. 500649/1984). In such a process, however, it is difficult to highly precisely adjust the water concentration in the vicinity of the enzyme to a suitably very low concentration, and therefore the industrialization of this process is obstructed.

As described above, an interesterification is caused by a combination of a hydrolysis and a synthesis. In a reaction system of interesterification, when the water concentration is high, water is consumed by a hydrolysis. That is, the water concentration in the reaction system is changing every moment with the proceeding of the reaction. Therefore, the determination of the water concentration in the beginning of the reaction is meaningless, and the constant adjustment of water concentration to a suitable concentration during the reaction is the important subject in an invention.

Moreover, in a process using an immobilized enzyme or microorganism (hereinafter referred to as "immobilized enzyme catalyst"), there is required a technique for constantly adjusting the water content held in the immobilized enzyme catalyst (hereinafter referred to as "water content of catalyst") to the optimum.

In almost all the conventional processes, however, attention is paid only to the water concentration at the beginning of the reaction and there is no suggestion about a method of adjustment of the water concentration to a suitable during the reaction. Such adjustment has been said to be technically difficult.

Since the starting materials of interesterification such as a triglyceride, a fatty acid and a fatty acid ester with a lower alcohol or solvents for dilution contains a small amount of water, a diglyceride or a monoglyceride is produced by a hydrolysis, when the starting material or the solvent is used without taking any measures. It is known that diglyceride forms an eutectic mixture with triglyceride to suppress the crystallization of triglyceride. And consequently, there arise problems that the yield of triglyceride as product is lowered, and that the quality of product is deteriorated. Therefore, a technique for carrying out the reaction with lowering the water concentration in the reaction system to a lower value was required.

For an industrialization of interesterification, it is an inevitable problem that the rate of reaction is increased by utilizing a high-cost immobilized enzyme catalyst as effectively as possible, and at the same time the yield and quality of the product are improved by suppressing the proceeding the hydrolysis. And there is desired a technique for determining the water concentration in catalyst suitable for a desirable reaction and for carring out a reaction efficiently with adjusting the water concentration to the determined suitable value constantly.

The object of the present invention is to provide a process for efficiently preparing valuable a fat or oil as described above.

SUMMARY OF THE INVENTION

It has now been found that although it is difficult to directly determine the water content of catalyst in a reaction system wherein a solid and a liquid coexist, there is a dynamic equilibrium relationship of water (adsorption isotherm) between reaction liquid and the immobilized enzyme catalyst and the water content of catalyst can be indirectly. calculated on the basis of the equilibrium relationship, by measuring the water concentration in the reaction liquid. Further, it has also been found that the water content of catalyst can be adjusted to the desired value as a result of an adjustment of the concentration of water in the reaction liquid by increasing or decreasing thereof to a value corresponding to the desired water concentration in catalyst, and thus the present invention has been accomplished.

According to the present invention, there is provided a process of an enzymatic interesterification in a low water content condition (hereinafter referred to as "microaqueous system"), which comprises subjecting a reaction liquid containing (a) a fat or oil and (b) a member selected from the group consisting of (i) another fat or oil, (ii) a fatty acid ester with a lower alcohol and (iii) a fatty acid to the action of a lipase in the form of an immobilized enzyme catalyst, with adjusting the water concentration in the reaction liquid during the reaction.

In employing the process of the present invention, it is preferable to predetermine the water concentration in the reaction liquid on the basis of the relationship between the water content of catalyst and the reaction rate or the product yield since the reaction rate or the product yield can reach the maximum value simply and efficiently by adjusting the water concentration in the reaction liquid to the predetermined water concentlation in the reaction liquid.

By employing the process of the present invention, it becomes easy to adjust the water content of catalyst to a certain value so that the reaction rate or the product yield can reach the maximum value. In addition, the process of the present invention can be applied to both batch reaction system and continuous reaction system, and the process is particularly suitable for a operation of long duration because the deactivation of enzyme is reduced.

As mentioned above, the process of the present invention is novel as the practical process wherein it is intended that the product is industrially produced as efficiently as possible manner by means of constantly adjusting the environment of enzyme to microaqueous condition so that the immobilized enzyme catalyst is effectively utilized and the product yield is increased satisfactorily.

DETAILED DESCRIPTION

In the present invention, paying attention to a dynamic equilibrium relationship of water between an immobilized enzyme catalyst and a reaction liquid in a microaqueous system, the dynamic equilibrium relationship is predetermined, then a water concentration in catalyst is obtained by a conversional calculation from a result of an analysis of very low water concentration in the whole reaction system or in the reaction liquid on the basis of the above mentioned dynamic equilibrium relationship.

The term "immobilized enzyme catalyst" used in the present invention means a microorganism itself having an enzyme in it, a microorganism which has an enzyme in it and is immobilized onto a carrier, and enzyme immobilized onto a carrier, and the like. Among the immobilized enzyme catalyst, dry microbid cells and immobilized dry microbial cells are preferable since those are economical and easily available, and since when the microbial cell is used, affinity between enzyme and substrate is high and the reaction rate is high, because cell membrane of the microbial cell has both hydrophobic and hydrophilic characteristics.

In the present invention, the term "reaction liquid" means substrate employed, i.e. a mixture of a fat or oil and another fat or oil, a mixture of a fat or oil and a fatty acid, or a mixture of a fat or oil and a fatty acid ester with a lower alcohol; or means a mixture of the above substrate and an organic solvent for diluting the substrate.

Figure 1:
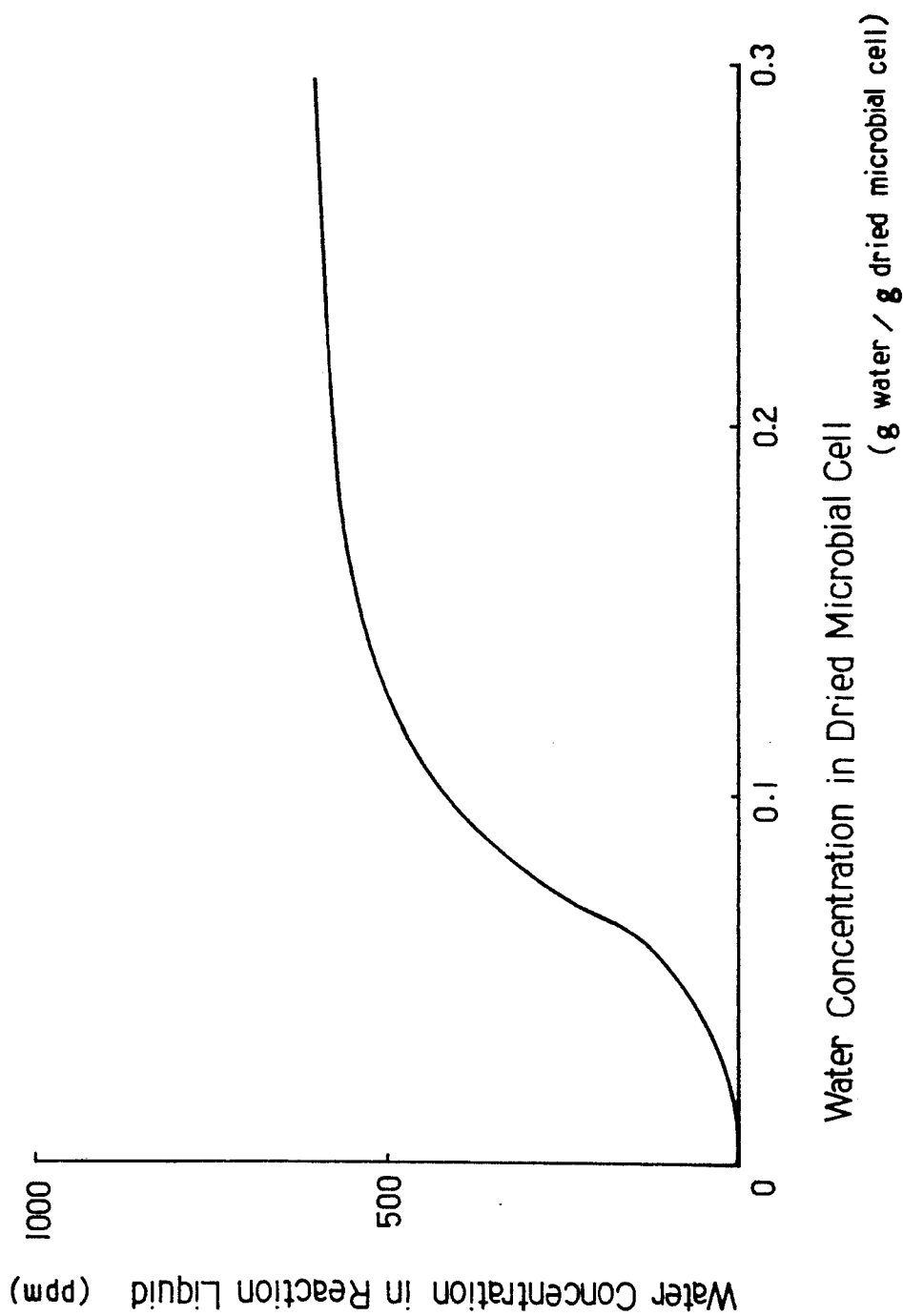
FIG. 1 is a graph showing a dynamic equilibrium relationship of water between a dried microbial cell and the reaction liquid obtained in Example 1.

The above mentioned dynamic equilibrium relationship depends on kinds and constitution of substrates and solvents for dilution, or depends on kinds of enzymes and microorganisms used for immobilized enzyme catalyst or kinds of carriers such as microorganism-supporting material and gelatinizing agent used for immobilization. Each combination of the above factors has a particular equilibrium relationship. The above equilibrium relationship can be easily obtained in accordance with a usual method for obtaining adsorption isotherm of a liquid phase adsorption. As an example, a dynamic equilibrium relationship of water between a reaction liquid and immobilized enzyme catalyst as shown in FIG. 1 is obtained.

When a dynamic equilibrium relationship is utilized, a water concentration in catalyst corresponding to a water concentration in a reaction liquid can be obtained even during the reaction by measuring the water concentration in a reaction liquid. If the water concentration in a reaction liquid is adjusted to a specified value, as a result, the water concentration in catalyst can be adjusted to a value corresponding to the above water concentration in a reaction liquid.

On the other hand, the effect of the water content of catalyst on the reaction rate and the product yield appears in various ways depending on kinds of carriers used for immobilization of enzyme, methods of immobilization, kinds, activities and specificities of enzymes, or kinds of substrates and solvents or mixing ratios thereof. The optimum water concentration in the above system can be easily determined in general in accordance with a usual method, and the optimum water concentration in a microbial cell is in a range from about 0.1 to about 20% by weight as a result of a study on various microorganisms. In order to adjust the water concentration in catalyst to the above mentioned range, it is required to adjust the water concentration in a reaction liquid to a very low level ranging from about 5 to about 1000 ppm, preferably from 10 to 500 ppm. And it is more preferable to adjust the water concentration in a reaction liquid to a value ranging from 10 to 200 ppm in order to suppress hydrolysis which is a side reaction and to improve the quality of the product.

As methods of analysing the water concentration in a reaction liquid, there are generally well known a gravimetric analysis wherein the water concentration in a sample is obtained from the change in weight after the water in the sample is vaporized, Karl Fischer's method wherein a dehydration reaction is utilized, and the like. In Karl Fischer's method, when a liquid sample is collected from the reactor, solid phase is separated by means of a suitable filter, for example, a porous filter made of sintered metal or resin, and the concentration of water in liquid phase is measured. As other methods than those described above, there can be utilized on-line type moisture analysers in accordance with various principles and a sensor for water concentration used in, for example, a method wherein a sample is irradiated with infrared rays and the quantity of absorbed rays are measured, a method wherein a measurement is carried out based on a change in electric resistance, a method wherein an electric capacity of liquid is measured, or the like. When the measured value of water concentration is smaller than the predetermined value, the concentration of water in the reaction liquid is increased. On the contrary, when the water concentration is larger than the predetermined value, the concentration of water in the reaction liquid is decreased. Thereby, the water concentration in catalyst can be constantly adjusted to a suitable concentration.

During the reaction, water in a reaction liquid is consumed by hydrolysis which is a side reaction. Therefore, in general, in an adjustment of the water concentration in reaction liquid, a small amount of water is added. However, when the adjusted water concentration is too high or when the concentration of by-product is to be further reduced, excess water in the reaction liquid is removed before or during the reaction to adjust the water concentration to a lower value.

As a method for increasing the water concentration in the reaction liquid, there can be utilized a method wherein water is injected directly into the reactor, a method wherein water is dissolved in a reaction liquid and the reaction liquid in which water is dissolved is injected into the reactor and the like. The above liquid to be injected may be one in water is dissolved in a fresh reaction liquid or may be the liquid in which water is dissolved in a reaction liquid collected from the reactor. Further, the liquid to be injected may be one saturated with dissolved water, or may be one which is not saturated with water and in which water is dissolved to some extent.

The reaction liquid can be saturated with water by contacting the reaction liquid with water for a long time. It is possible to make a reaction liquid in which water is dissolved to some extent by adjusting the contacting time of the reaction liquid with water in accordance with the dissolving rate. Further, the adjustment of the water concentration in the reaction liquid to be injected can be carried out by another method wherein an aqueous solution of a water soluble substance is contacted with the reaction liquid and the dynamic equilibrium relationship of water between the reaction liquid and the aqueous solution of the water soluble substance is utilized. The above water soluble substance and the reaction liquid are not soluble in each other. Examples of such water soluble substance are, for instance, glycerin, ethylene glycol, diethylene glycol, triethylene glycol, propylene glycol, butylene glycol, hexylene glycol, polyethylene glycol, and the like.

As a method for reducing the water concentration in the reaction liquid, there are utilized a method wherein a fresh reaction liquid from which water is removed or partially removed is directly injected into the reactor, a method wherein the reaction liquid collected from the reactor is returned to the reactor after water is removed completely or partially from the collected reaction liquid, and the like.

As a method for removing water completely or partially from an organic solvent system such the reaction liquid in the present invention, a method wherein the reaction liquid is brought into contact with a substance having water-absorbing capability can be adopted. As the substance having water-absorbing capability, any substance which is not soluble in the reaction liquid and does not react with the substrate can be employed. Examples of such substance are, for instance, a water soluble substances such as glycerin, ethylene glycol, diethylene glycol, triethylene glycol, propylene glycol, butylene glycol, hexylene glycol and polyethylene glycol; water-absorptive substances such as molecular sieve, zeolite, silica gel, alumina, diatomaceous earth, activated carbon, kaolinite, perlite, cellulose powder, hydroxyl apatite and chitosan; monosaccharides such as glucose, galactose, ribose and fructose; polysaccharides such as sucrose, trehalose, dextrin, glycogen and starch; salts having water-absorbing capability such as calcined gypsum, calcium carbonate and calcium chloride; deliquescent salts such as sodium hydroxide and calcium hydroxide; metal salts without crystallization water such as anhydrous sodium sulfate; and the like.

As a unit for adjusting water concentration as described above, any type of unit such as a stirred tank type unit and a packed layer type unit can be employed. Also there can be employed a membrane type unit wherein flows of the reaction liquid and water or aqueous solution of the above water-soluble substance are provided respectively on the both side of a thin film or on inner and outer side of a tube, made of water hydrophobic or hydrophilic porous resin.

Though a type of the reaction in the present invention may be a batch reaction type or a continuous reaction type, it is advantageous to apply the process of the present invention particularly to a continuous reaction lasting for a long period, because the deactivation of enzyme is reduced by employing the present invention. In addition, though the number of stages of the reactor may be one, a multistage type reactor may be employed in order to increase the yield. Further, a type of the reactor may be any type among a stirred tank type, a fluidized bed type, a packed layer type and a combined type in which these types are combined together. When the packed layer type is used among the above reacting apparatuses, it is preferable that, for an efficient reaction, the reactor is devided into some stages and the number of stages is increased in order to prevent the water supplied from being selectively absorbed by enzyme located around an inlet of the reactor.

Hereinafter, embodiments of reactor in accordance with the present invention are explained referring to FIGS. 2 through 7. However, it would be understood that the present invention is not limited to the embodiments.

Figure 2:
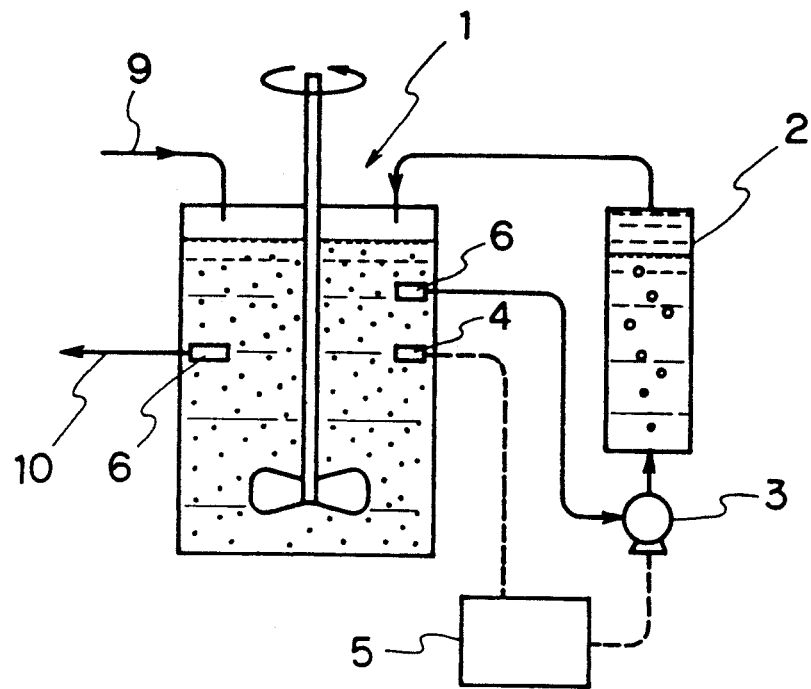
FIG. 2 to FIG. 7 show illustrations of embodiments of reaction apparatus used in the process of the present invention.

FIG. 2 is a schematic view of an reacting apparatus in which a reactor comprising a single stage stirred tank and a water dissolution unit comprising a tower filled with water are combined together.

FIG. 2 is an illustration of one embodiment of the reacting apparatus used in the process of the present invention, which is equipped with a reactor 1 comprising a single stage stirring tank, a water dissolving unit 2 comprising a tower filled with water, a circulating pump 3, a water concentration sensor 4 for detecting a change in the water concentration by measuring a change of an electric resistance, a processor 5 for calculating a difference between the detected water concentration and a predetermined certain value and for providing output signal to control the flow rate of the pump, a filter 6 made of sintered metal for removing the immobilized enzyme catalyst from the cerculated reaction liquid, a reaction liquid inlet 9 and a reaction liquid outlet 10.

In the above apparatus, the reactor 1 and the water dissolving unit 2 are connected by means of stainless pipes as a path for the reaction liquid via the circulating pump 3 and the filter 6. Further the reactor 1 and the circulating pump 3 are connected by a signal line, via the water concentration sensor 4 and the processor 5.

First, the reactor 1 is filled with the reaction liquid from the inlet 9. Then, microbial cells, enzymes derived from the microbial cells or immobilized enzymes therefrom are added thereto and interesterification is commenced. The concentration of water in the reaction liquid is constantly measured by the water concentration sensor 4, and the measured value and the predetermined value are compared in the processor 5, then the circulating pump 3 is controlled, thus the water concentration in the reaction liquid is maintained at a predetermined certain value.

That is, when the obtained water concentration becomes lower than the predetermined value, the reaction liquid collected from the reactor 1 by the circulating pump 3 is supplied to the water dissolving unit 2 where water is dissolved in the reaction liquid, and the reaction liquid wherein the water is dissolved is circulated to the reactor 1 in order to increase the water concentration in the reaction liquid in the reactor 1. Thereby, the water content of catalyst can be constantly maintained at a required suitable value.

Thus the continuous reaction is allowed to proceed while the water concentration in the reaction liquid is adjusted so that the reaction rate of interesterification reaches the maximum value. The product is separated in an ordinary manner such as column separation or crystallization operation after the reaction liquid is collected from the reaction liquid outlet 10.

Figure 3:
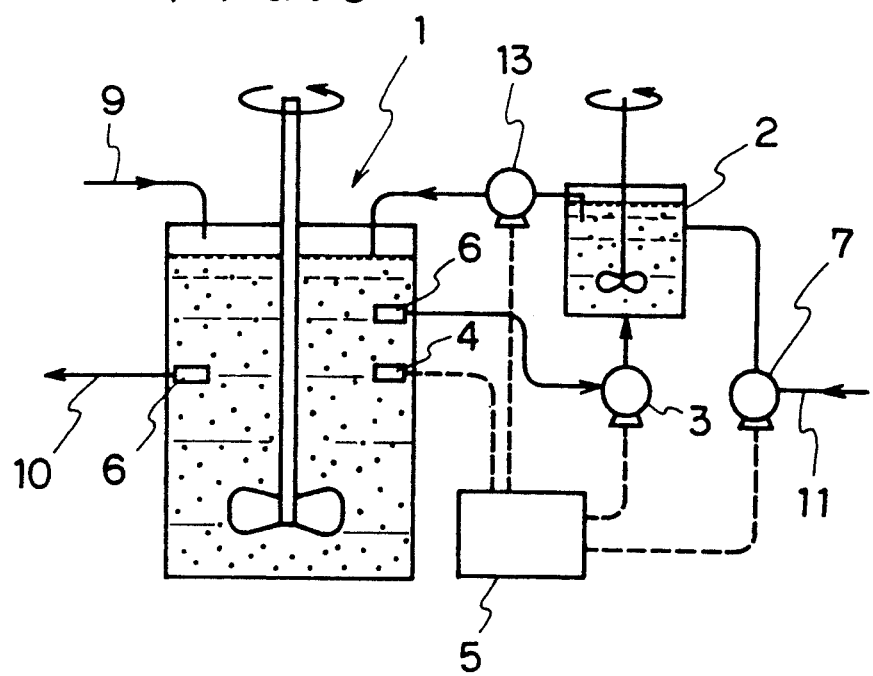

FIG. 3 is a schematic view of a reaction apparatus in which a reactor of a single stage stirred tank is combined with a water dissoving unit of a stirred tank type.

In the apparatus shown in FIG. 3, a water dissolving unit 2 comprises a stirred tank which holds the reaction liquid, and water addition nozzle 11 is connected with the water dissolving unit 2 via water adding pump 7.

In case that water is directly injected to the reactor in such a manner as taken in the apparatus shown in FIG. 2, there is a possibility that the water content of catalyst is not uniform because the water concentration in the reaction system is very low. By using the apparatus shown in FIG. 3, water is injected to the reactor 1 after the water is dissoved in the reaction liquid in the water dissolving unit 2.

First the water concentration in the reaction liquid is constantly measured by a water concentration sensor 4 in the same manner as taken in the apparatus shown in FIG. 2. Then the measured value and the predetermined value are compared in the processor 5, and a circulating pump 3, a circulating pump 13 or the water adding pump 7 is started or stopped in order to adjust the flow of the reaction liquid in which injected water is dissolved. Thus the water concentration in the reaction liquid in reaction system is maintained at the predetermined value.

That is, when the measured water concentration becomes lower than the predetermined value, the reaction liquid collected from the reactor 1 by the circulating pump 3 is supplied to the water dissolving unit 2, and at the same time, water is added by the water adding pump 7, then the required amount of the reaction liquid in which water is dissolved is transmitted to the reactor 1 in order to increase the water concentration in the reaction liquid in the reactor 1. Thereby, the water content of catalyst can be constantly maintained at a required suitable value.

Thus, a continuous reaction is allowed to proceed and the product is separated in the same manner as taken in the apparatus shown in FIG. 2.

Figure 4:
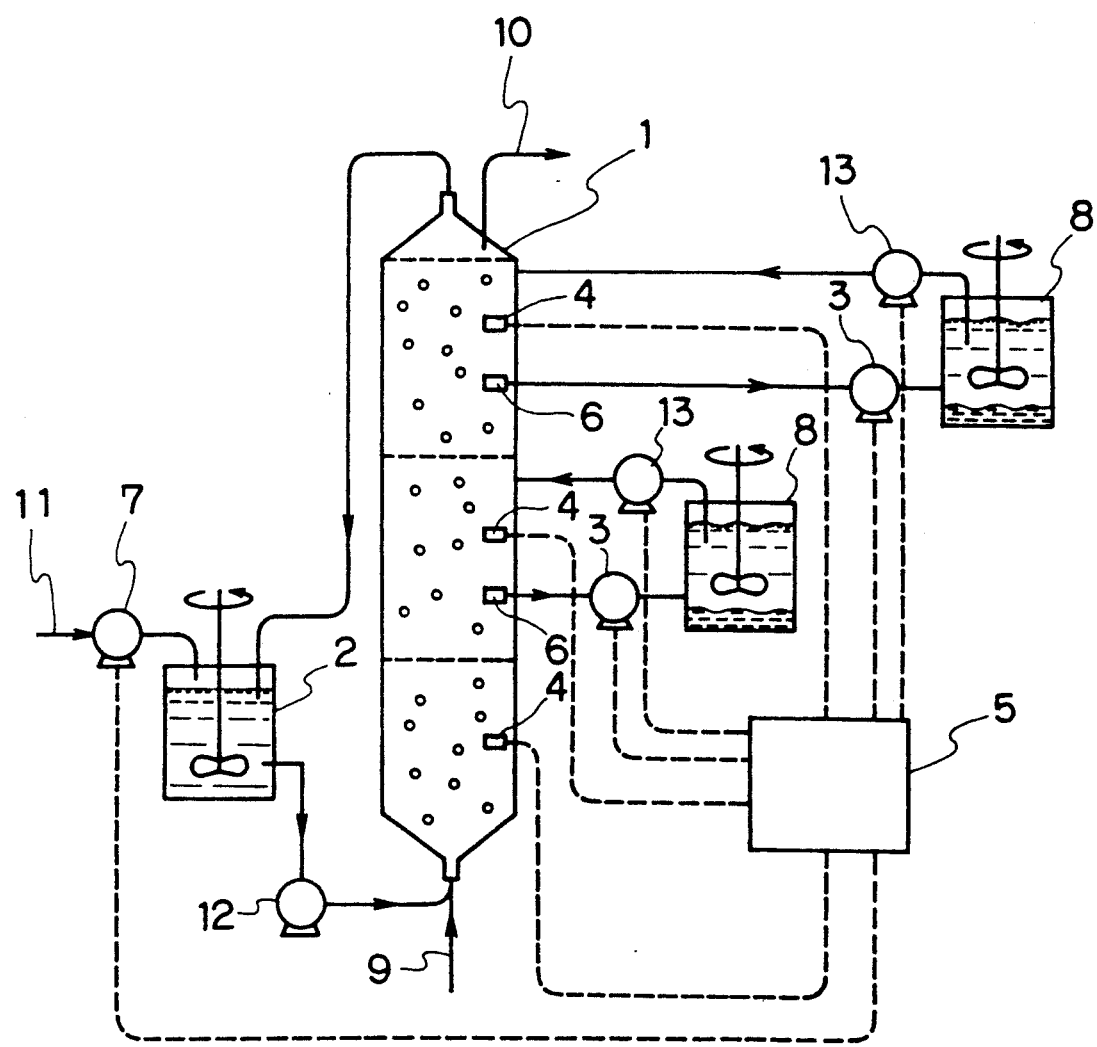

FIG. 4 is a schematic view of a reaction apparatus in which a multi-stage fluidized bed is used as a reactor and each stage of the reactor is connected with a moisture adjusting unit of a stirred tank type.

In the apparatus shown in FIG. 4, a reactor 1 comprises a multi-stage fluidized bed, and each stage of the reactor 1 and each moisture adjusting unit 8 are connected via each circulating pump 3 and 13. In the moisture adjusting unit 8, an aqueous solution of a water soluble substance is brought into contact with the reaction liquid. The above water soluble substance and the reaction liquid are not soluble each other In the apparatus shown in FIG. 4, the reactor 1 is multi-stage type and a circulating pump 12 is operated at all times in order to allow the catalyst to be fluidized in the reactor 1. The water concentration in the first stage, which is the lowest stage in the reactor 1, is increased by supplying water to a water dissolving unit 2 via a water adding nozzle 11 by water adding pump 7. In addition, each of the second stage and the third stage is connected to the water concentration adjusting unit 8 via the circulating pump 3. In the water concentration adjusting unit 8, an aqueous solution of glycerin and the reaction liquid are stirred so calmly that the formation of water droplets is prevented. Thus the aqueous solution of glycerin and the reaction mixture are brought into contact with each other. By utilizing the dynamic equilibrium relationship between the reaction liquid and the aqueous solution of glycerin, water in the aqueous solution of glycerin is dissolved in the reaction liquid, or water in the reaction liquid is removed by the aqueous liquid of glycerin, and thereafter the reaction liquid is returned to the reactor. Thereby, the water concentration in the reaction liquid is adjusted very minutely.

In this connection, in the above moisture adjusting unit 8, if the water concentration in the reaction liquid is higher than the concentration at the equilibrium state, excess water is absorbed in the aqueous solution of glycerin in accordance with the dynamic equilibrium relationship between the aqueous solution of glycerin and the reaction liquid. On the contrary, if the water concentration in the reaction liquid is lower than the concentration at the equilibrium state, the required amount of water is supplied from the aqueous solution of glycerin.

The water concentration in the reaction liquid is always measured by a water concentration sensor 4 in the same manner as taken in the apparatus shown in FIG. 2. Then the measured value and the predetermined value are compared in a processor 5, and a circulating pump 3, a circulating pump 13 or the water adding pump 7 is started or stopped in order to dissove water in the reaction liquid or remove water from the reaction liquid. Thus the water concentration in the reaction liquid is adjusted to the predetermined value constantly.

That is, when the water concentration measured at each stage becomes lower than the predetermined value, the reaction liquid in which water is dissolved by adding water to the water dissolving unit 2 by means of the water adding pump 7 is transmitted to the first stage of the reactor 1 by using the circulating pump 12 and the reaction liquid which is collected from the reactor 1 by means of the circulating pump 3 and which is supplied to the moisture adjusting unit 8 where the water concentration is adjusted is transmitted to the second and the third stages of the reactor 1 by using the circulating pump 13. Thus the water concentration in the reaction liquid in the reactor is increased or decreased and the water content of catalyst at each stage can be constantly maintained at the required suitable value.

Thus, a continuous reaction is allowed to proceed and the product is separated in the same manner as taken in the apparatus shown in FIG. 2 and described in the above explanation of FIG. 2.

Figure 5:
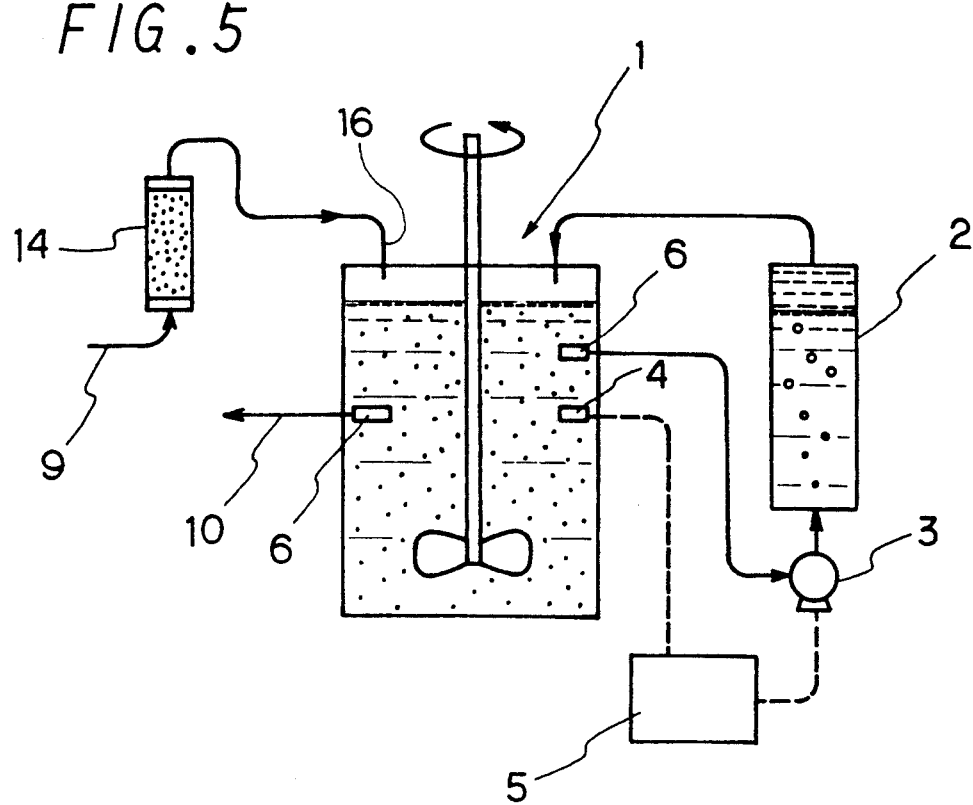

FIG. 5 is a schematic view of a reaction apparatus in which a reactor comprising a single stage stirred tank as shown in FIG. 2 and a water dissolving unit comprising a tower filled with water as shown in FIG. 2 are combined with a water removing unit comprising a packed column of calcium chloride.

The reacting apparatus shown in FIG. 5 is provided with a water removing unit 14 comprising a packed column of calcium chloride between the reactor 1 and the reaction liquid inlet 9. In this system, the reaction liquid being passed through the water removing unit 14 where water is removed or partially removed is added to the reactor 1 via the reaction liquid inlet 16. And the water concentration in the reaction liquid is measured at all times by a moisture sensor 4 in the same manner as taken in the apparatus shown in FIG. 2. Then the measured value and the predetermined value are compared in a processor 5, and the circulating 3 is started or stopped. Thus the water concentration in the reaction liquid is maintained at the predetermined value.

Thus a continuous reaction is allowed to proceed and the product is separated in the same manner as taken in the apparatus shown in FIG. 2.

Figure 6:
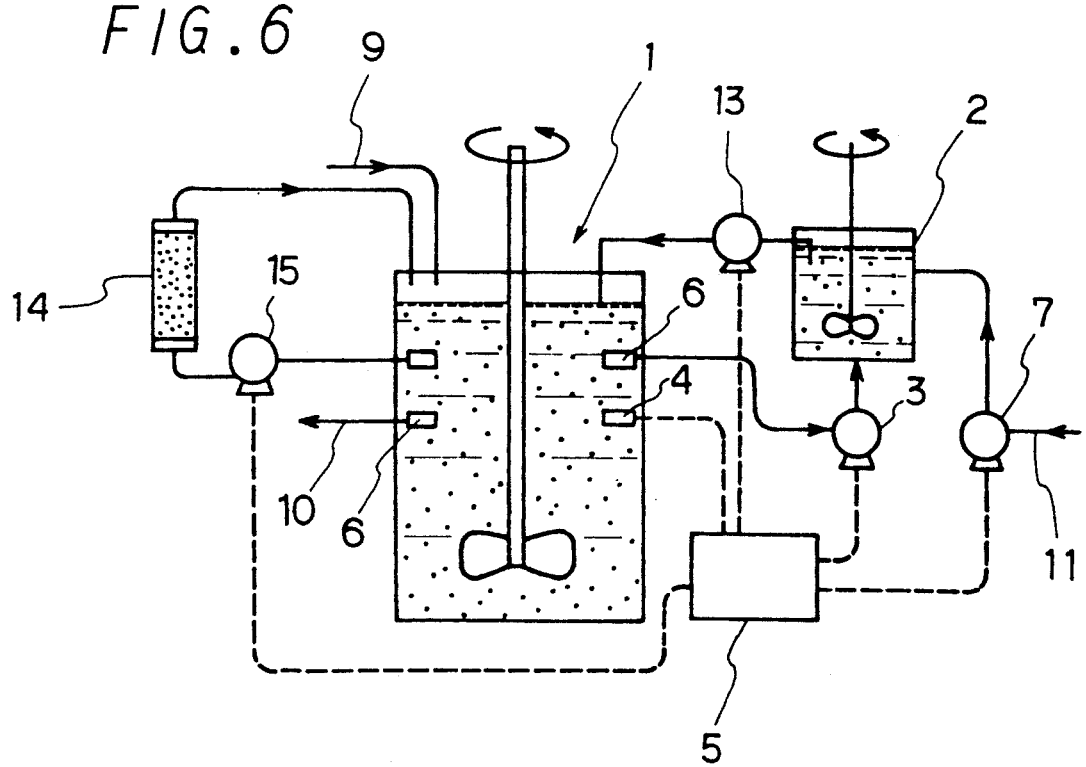

FIG. 6 is a schematic view of a reacting apparatus in which a reactor comprising a single stage stirred tank as shown in FIG. 3 and a water dissolving unit comprising a stirred tank type as shown in FIG. 3 are combined with a water removing unit comprising a packed column of silica gel.

In the apparatus shown in FIG. 6, a reactor 1 is connected to a water dissolving unit 2 via a circulating pump 3 and also connected to a water removing unit 14 via a circulating pump 13.

In the apparatus shown in FIG. 6, the water concentration in the reaction liquid is measured at all times by a moisture sensor 4 in the same manner as taken in the apparatus shown in FIG. 3. Then the measured value is compared with the predetermined concentration having some allowable range in a processor 5. When the measured value is lower than the lowest allowable limit of the predetermined concentration, a water adding pump 7 and circulating pumps 3 and 13 are started to increase the water concentration in the reaction liquid. On the contrary, when the measured value is higher than the highest allowable limit of the predetermined concentration, a circulating pump 15 is started to remove water and to reduce the water concentration in the reaction liquid. Thus the water concentration is constantly maintained within the required suitable range of the water concentration with a satisfactory accuracy.

Thus a continuous reaction is allowed to proceed and the product is separated in the same manner as taken in the apparatus shown in FIG. 2.

In case that the apparatus shown in FIG. 5 and FIG. 6 are used, the water concentration can be adjusted more minutely compared with the case wherein the apparatuses shown in FIG. 2 and FIG. 3 are used, and therefore, side reaction, i.e. hydrolysis is suppressed, and the yield and the quality of the product obtained as a result of interesterification can be improved.

Figure 7:
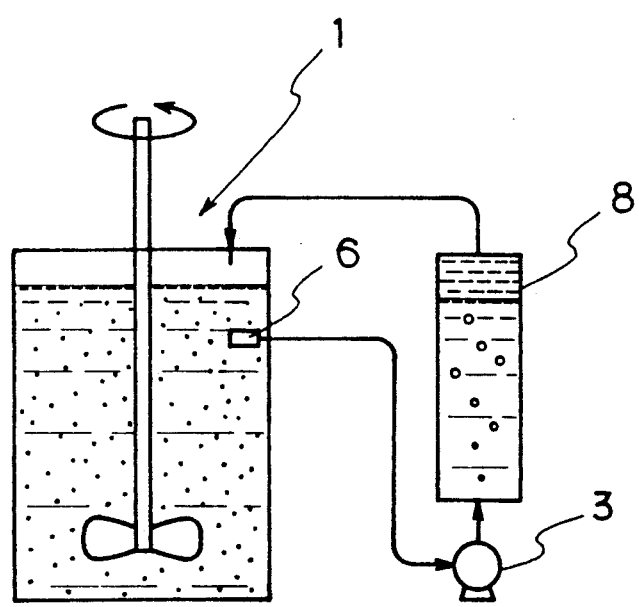

FIG. 7 is a schematic view of a reacting apparatus in which a reactor comprising a single stage stirred tank is combined with a moisture adjusting unit comprising a packed column of aqueous solution of glycerin.

In the apparatus shown in FIG. 7, a reactor 1 is connected to a moisture adjusting unit 8 via a circulating pump 3. The reaction liquid is always circulated between the reactor 1 and the moisture adjusting unit 8 by the circulating pump 3, and the water concentration in the circulated reaction liquid is maintained at the predetermined value by virtue of the dynamic equilibrium relationship of water between the aqueous solution of glycerin and the reaction liquid. In the moisture adjusting unit 8, by changing the composition of the aqueous solution of glycerin which contacts with the reaction liquid, the water concentration in the reaction liquid can be adjusted to any desired value in accordance with the dynamic equilibrium relationship. Therefore, the aqueous solution of glycerin serves both for adding water and for removing water.

That is, when the water concentration in the reaction liquid is higher than the concentration at the equilibrium state, the excess water is absorbed by the aqueous solution of glycerin. On the contrary, when the water concentration in the reaction liquid is lower than the concentration at the equilibrium state, the required amount of water is supplied from the aqueous solution of glycerin. Thus the water concentration in the reaction liquid is maintained at a predetermined value in the moisture adjusting unit 8 in accordance with the dynamic equilibrium relationship. As a result, in the reactor, the water content of catalyst can be constantly maintained at the predetermined concentration in accordance with the partition equilibrium relationship between water concentration in the reaction liquid and water content of the catalyst.

Thus a continuous reaction is allowed to proceed and the product is separated in the same manner as taken in the apparatus shown in FIG. 2.

The apparatus shown in FIG. 7 is an example in which the water concentration is adjusted to a predetermined value without using a moisture sensor. In the moisture adjusting unit 8 in this apparatus, the water concentration in the reaction liquid is adjusted to a value corresponding to the water concentration of the aqueous solution of glycerin in accordance with the dynamic equilibrium relationship between the aqueous solution of glycerin and the reaction liquid. And the above reaction liquid is always circulated between the moisture adjusting unit 8 and the reactor 1. As a result, the concentration of water in the catalyst in the reactor 1 is maintained at a predetermined value.

Further, in the apparatuses shown in FIGS. 2 to 6, the water concentration in the reaction liquid in the reactor 1 is always measured by the water concentration sensor 4, and the pump is started or stopped while comparing the measured value with the predetermined value in the processor 5, then the water concentration in the reaction liquid is adjusted to the specified value by controlling the flow rate. As a result, the water content of catalyst is maintained at a predetermined value.

With respect to the lipase used in the present invention, the origin thereof is not limited. However, positional specificity and substrate specificity of enzyme differs depending on the origin thereof, and therefore, products having high purity can be produced at will by utilizing the above specificities.

For example, when using enzymes originated from *Candida rugosa*, *Corynebacterium acens*, *Staphylococcus aureus*, or the like which hardly shown specificities, interesterification can be carried out in triglyceride at the 1-, the 2- and the 3-positions at random. When using enzyme originated from *Geotrichum candidum* which selectively release only long chain fatty acid having cis double bond at the C9-position from triglyceride, only the above acyl residue in triglyceride can be exchanged with another acyl residue. Further, when interesterification is carried out with using an enzyme originated from *Aspergiuus niger*, *Mucor javanicus* or a microorganism belonging to genus Rhizopus, which has a specificity to act only on the 1- and the 3-positions in triglyceride, it is possible to exchange acyl residue only at the 1- and the 3-positions with other acyl residue while acyl residue at the 2-position is unchanged. As an example of utilizing enzyme of the above mentioned kind, there can be exemplified the production of substitutional fats for cacao butter including in a large amount of SOP (1-stearoyl-2-oleyl-3-palmitoyl-glycerol) in which stearic acid and palmitic acid are bonded to the 1- and the 3-positions respectively.

In using the above mentioned enzyme, it is industrially preferable that immobilized enzyme catalyst is prepared with the enzyme in accordance with various immobilizing method so that the immobilized enzyme catalyst can be re-used or continuously used in order to reduce the consumption of the expensive enzyme. As a method for immobilizing enzyme, there can be exemplified an adsorption method using carriers such as Celite, activated alumina, activated clay, diatomaceous earth and activated carbon; an entrapping method using polyurethane resins, carageenan, sodium alginate or photocrosslinking resin; and cross-linking method in which enzyme is immobilized onto a carrier using various cross-linking agents. Any method among those mentioned above can be used in the present invention.

The enzyme used in the present invention can be a purified enzyme, or a crude enzyme which is obtained by salting-out the culture solution, or the like.

The enzyme used in the present invention is not limited to enzyme which is extracted from a microbial cell, and there can be also used a microbial cell itself containing lipase. When the microbial cell is used, affinity between enzyme and substrate is high and the reaction rate is high, because cell membrane of the microbial cell has both hydrophobic and hydrophilic characteristics. In addition, as the microbial cell, a cultured cell itself can be used, and there can be used microbial cell immobilized in accordance with the same immobilizing method as described above or in accordance with a method wherein microbial cell is immobilized onto porous material having a sponge or network structure. Particularly when the latter method is employed, no gelatinizing agent is required in contrast with the entrapping method in which a gelatinizer is used. And the latter method has advantages including the fact that the reaction rate is high. Therefore, the latter method provides industrially advantageous process. As the above mentioned porous material, there can be used a material having a shape of block or sphere made of metal or polymer resin. As the metallic porous material, there is exemplified a particle formed by winding a metallic fiber such as stainless steel, iron or aluminum. As the polymeric porous material, there are exemplified addition polymer materials such as polyolefines, diene polymers and vinyl polymers; condensation polymer materials such as polyether, polyester and nylon; or materials such as silicone resins and fluoro resins. For example, there can be used material made of polyurethane foam commercially available from Kabushiki Kaisha Bridgestone under the trade name of HR-40. In order to immobilize microorganisms satisfactorily, porous material having a porosity of 60 to 99%, the number of pores per unit straight line length is 2 to 50 /cm, and an outline dimension is 1 to 20 mm is prefereable to use, among the above mentioned porous materials.

Further, it is desirable to adjust the water content of catalyst to some extent prior to the reaction for the purpose of an effective adjustment during the reaction including the initial stage thereof. When the excess water is removed, the removal of the excess water can be carried out by extracting water by means of soaking the catalyst with acetone or aqueous solution of acetone, or by drying the immobilized enzyme catalyst under reduced pressure at need.

As the substrate used in the present invention, a mixture of a fat or oil and another fat or oil, a mixture of a fat or oil and a free fatty acid having 8 to 24 carbon atoms, or a mixture of a fat or oil and an ester of the above fatty acid with a lower alcohol having 1 to 3 carbon atoms can be used.

As the above fat or oil, there can be used a fat or oil such as palm oil, olive oil, coconut oil, sheafat, fish oil or tea oil. A mixture thereof can be also employed.

As the fatty acid, there can be exemplified saturated fatty acids such as caprylic acid, capric acid, palmitic acid, stearic acid and behenic acid; and unsaturated fatty acids such as palmitoleic acid, oleic acid, linoleic acid and linolenic acid. The above fatty acids may be used alone or the above fatty acids can be used as a mixture thereof. As the fatty acid ester with an alcohol, there can be used an ester of the above-mentioned fatty acid with a lower alcohol, for example, an ester of the above fatty acid with methyl alcohol, with ethyl alcohol or with propyl alcohol.

Further in the present invention, the above substrate can be used as it is, or the above substrate can be used after the substrate is diluted at need with organic solvents such as n-hexan, isooctane, acetone, ethanol, methanol and petroleum ether.

The process of the present invention relates to a process for carrying out an interesterification with employing lipase by utilizing a reversible reaction of hydrolysis and in a low water content condition. In the process of the present invention, water is suitably supplied to the reaction system in which water is consumed by the hydrolysis, especially to the immobilized enzyme catalyst so that the water content of the catalyst is constantly adjusted to a suitable very low concetnration, at which the activity of the enzyme is effectively utilized and formation of by-product of side-reaction is suppressed. Thus the process of the present invention contributes to industrial application of such reaction. According to the present invention, the reaction can be achieved not only by means of batch reaction, but also by means of continuous reaction which has been regarded as difficult because of the inactivation of the enzyme by consumption of water.

The process of the continuous reaction according to the present invention has advantages that the production rate of product is high and an energy saving can be attained, and that the concentration of the by-product can be decreased, in comperison with the batch reaction. Therefore, the load of refining the product can be reduced, and moreover the yield and quality of the product is improved in the continuous interesterification.

Accordingly, since the process of the present invention can adjust suitably the water concentration of reaction system, expensive enzyme can be effectively utilized and great profit is brought into the field of the biochemistry.

The present invention is more specifically described and explained by means of the following Examples. It is to be understood that the present invention is not limited to the Examples, and various changes and modifications may be made in the invention without departing from the spirit and scope thereof.

EXAMPLE 1

To the reaction liquid containing 1 part by weight of olive oil, 2 parts by weight of methyl stearate and 3 parts by weight of hexane was added 0.5 part by weight of dried cells of *Rhizopus chinensis* IFO 4768 to carry out, an interesterification, with detecting the water concentration in the reaction liquid by means of a moisture sensor and adjusting the water concentration in the reaction liquid.

The microorganism employed was cultured at 30° C. for 40 hours in a culture medium obtained by dissolving 7 parts by weight of peptone, 2 parts by weight of glucose, 0.1 part by weight of potassium dihydrogenphosphate, 0.1 part by weight of sodium nitrate and 0.05 part by weight of magnesium sulfate in 100 parts by weight of water with maintained the pH value in the culture medium at 5.6. After completion of the culture, the culture broth was filtrated to separte the cultivated cells from the culture medium, and the obtained cells were soaked with 5 parts by weight of acetone per 1 part by weight of the cells two times. Semi-dried cells obtained by refiltrating were dried for 2 hours under reduced pressure to obtain dried cells. The water concentration in the obtained dried cells was 8.0% by weight.

Separately, the same cultivated cells before abovementioned drying operation were inactivated by heating, and dried in accordance with above-mentioned manner to prepare inactivated dried cells. The obtained inactivated dried cells were mixed with the above-mentioned reaction liquid, and the dynamic equilibrium relationship of water between the reaction liquid and the inactivated dried cells was investigated. In order to investigate the dynamic equilibrium relationship, several preparations of mixture systems of 3.0 parts by weight of the inactivated dried cells and 100 parts of the above-mentioned reaction liquid are prepared. To each of the mixtures was added water in an amount of 0 to 1 part by weight, and the mixtures were stirred for 3 to 24 hours to reach an equilibrium state and then the water concentration in the each reaction liquid was analysed by means of Karl Fischer's method. The amount of water absorbed in the dried cells was calculated from the difference between the amount of added water and the amount of water contained in the reaction liquid. The obtained dynamic equilibrium relationship of water between the reaction liquid and the dried cells is shown in FIG. 1.

On the other hand, to 3.0 parts by weight of abovementioned dried cells was added 100 parts by weight of the above-mentioned reaction liquid and the interesterification was carried out in a batch type stirred tank while adjusting the water concentration in the reaction liquid.

The water concentration in the reaction liquid was analysed by means of a moisture analyzer (hygrometer) made by PANAMETRICS INC. (trade name: SYSTEM1) and was maintained at a certain value by adding water. The water content of the cells was calculated from the value of water concentration in the reaction liquid prepared as above and the dynamic equilibrium relationship shown in FIG. 1. The composition of the reaction liquid was analyzed by means of a liquid chromatography to measure a decreasing rate of triolein content in the olive oil.

The liquid chromatography analysis was carried out with using a eluent (acetonitrile : chloroform=7: 3) at a flow rate of 1 ml/min and at a temperature of 30° C. to separate the components. The column used was one made by Merck Co., Inc. (trade name: Lichrospher 100Rp-18 (4 mm×250 mm, particle size of packing: 5 μm)). The eluate were analyzed by means of a refractive index detector RI. As a result, the components were triolein, 1-stearoyl-2,3-dioleyl-glycerol and 1,3-distearoyl-2-oleyl-glycerol.

From the result of the investigation of the decreasing rate of the triolein component in the olive oil by means of the batch type reactor, it was found that in order to increase the rate of interesterification, it was preferable to adjust the water content of the dried cells at 8.0% by weight, or in other words, it was preferable to adjust the water concentration in the reaction liquid to 300 ppm.

The reaction liquid having the same composition as the above-mentioned reaction liquid was let flow into a reactor in the reacting apparatus as shown in FIG. 2 and was subjected to a continuous interesterification so that the mean residence time in the reactor was one hour. The used reactor 1 of stirred tank type had an inner diameter of 6 cm and a height of 15 cm and a water dissolving unit 2 was a cylindrical tower having an inner diameter of 3 cm and a height of 10 cm which was filled with water. The water concentration in the reaction liquid was detected by means of the above-mentioned moisture sensor, and was adjusted by starting or stopping a circulating pump 3. The reaction was carried out at a temperature of 40° C. and at a stirring rate of 350 rpm, with adjusting the water concentration in the reaction liquid to 300 ppm constantly.

The triglyceride composition was analysed in the above-mentioned manner and the concentrations of the desired product 1,3-distearoyl-2-oleyl-glycerol (hereinafter referred to as "SOS") in the reaction liquid were determined 0.5, 1, 4, 10 and 20 days after from the starting of the interesterification. The obtained values are shown in Table 1.

EXAMPLE 2, 3 and COMPARATIVE EXAMPLE 1

In Example 2, the interesterification of the reaction liquid was carried out with employing the same dried cells and same reaction liquid as in Example 1 under the same condition as in Example 1 with adjusting the water concentration in the reaction liquid to 150 ppm constantly.

In Example 3, the procedure of Example 2 was repeated except that the water concentration was adjusted to 500 ppm instead of 150 ppm.

In Comparative Example 1, the procedure of Example 2 was repeated except that the water concentration in the reaction liquid was not adjusted.

The concentration of the desired product SOS was analyzed in the same manner as in Example 1, and the results are shown in the Table 1.

As is apparent from Table 1, the productivity of the product in Example 1 in which the reaction liquid was subjected to the reaction with adjusting the water concentration of the reaction liquid to 300 ppm, was the highest compared with the productivities in Comparative Example 1 and Examples 2 and 3. When the adjusted water concentration was too high as in Example 3 or was too low as in Example 2, the productivity was lowered. When the continuous reaction was carried out without adding water as in Comparative Example 1, after some time, the reaction did not proceed any more. However, when the reaction was carried out with adding water to adjust the water concentration, the products having an almost constant concentration of the SOS could be produced even after the second day and for twenty days.

TABLE 1

| | Concentration of product SOS in reaction liquid (mol/l) | | | | |
|---|---|---|---|---|---|
| | 0.5 day | 1 day | 4 days | 10 days | 20 days |
| Example No. | | | | | |
| 1 | 0.028 | 0.033 | 0.033 | 0.032 | 0.031 |
| 2 | 0.020 | 0.020 | 0.021 | 0.020 | 0.020 |
| 3 | 0.019 | 0.026 | 0.022 | 0.021 | 0.020 |
| Comparative Example | | | | | |
| 1 | 0.020 | 0.025 | 0.004 | — | — |

EXAMPLE 4

To the reaction liquid containing 1 part by weight of olive oil, 2 parts by weight of methyl stearate and 3 parts by weight of hexane was added 0.5 part by weight of immobilized enzyme catalyst prepared by adsorbing a enzyme derived from *Rhizopus delemar* on Celite. And an interesterification was carried out with detecting the water concentration in the reaction liquid by means of a moisture sensor and adjusting the water concentration in the reaction liquid.

As shown in FIG. 3, the employed reactor 1 was stirred tank type (inner diameter 6 cm × height 15 cm) of one stage, and the employed water dissolving unit 2 was also stirred tank type (inner diameter 4 cm × height 8 cm). In order to adjust the water concetnration in the reaction liquid, the reaction liquid was constantly circulated and a required amount of water was added to the water dissolving unit and dissolved in the reaction liquid.

The immobilized enzyme catalyst was prepared by the following procedure. As a raw material, the enzyme (made by Seikagaku Kogyo Kabushiki Kaisha) derived from *Rhizopus delemar* was employed. There was dissolved 0.3 part by weight of the enzyme in 10 parts by weight of water. And thereto, 2 parts by weight of Celite was added, and then 50 parts by weight of acetone was added to precipitate the enzyme on the surface of Celite. To the immobilized enzyme catalyst obtained by filtration of the above mixture was added 50 parts by weight of acetone, and thereby the excess water in the immobilized enzyme catalyst was extracted by the acetone. Then the mixture was filtrated again to give a semi-dried immobilized enzyme catalyst, which was further dried under reduced pressure for 24 hours to obtain a dried immobilized enzyme catalyst. The water concentration in the obtained dried immobilized enzyme catalyst was 3.0% by weight.

Then, the dynamic equilibrium relationship of water the reaction liquid and the immobilized enzyme catalyst, and the relationship between the reaction rate and the water concentration in catalyst was investigated in the same manner as in Example 1. On the basis of the results of the above investigations, the interesterification of the reaction liquid was carried out with adjusting the water concentration in catalyst at 3.5% by weight and adjusting the water concentration in the reaction liquid at 280 ppm so that the reaction rate reaches the maximum value. The analysis of the triglyceride composition was carried out in the same manner as in Example 1, and the concentration of product SOS in the reaction liquid determined 0.5, 1, 4, 10 and 20 days after from the starting of the interesterification and the values are shown in Table 2.

COMPARATIVE EXAMPLE 2

A continuous interesterification was carried out with employing the same immobilized enzyme catalyst as in Example 4 and under the same reaction condition as in Example 4, without adding water at all. The concentration of the desired product SOS in the reaction liquid was analyzed in the same manner as in Example 1 and the results are shown in Table 2.

As in apparent from Table 2, the concentration of product SOS in the reaction liquid in Example 4, in which the water concentration in the reaction liquid was adjusted obtained at an almost constant concentration in the reaction liquid even after the second day and for twenty days. On the contrary, the concentration of product SOS in the reaction liquid in Comparative Example 2, in which the water concentration was not adjusted, decreased gradually. From the results, it is understood that the productivity of product in Example 4, in which the continuous reaction was carried out with adjusting the water concentration was higher than that in Comparative Example 2 in which the reaction was carried out without adding water at all.

TABLE 2

| Example No. | Concentration of product SOS in reaction liquid (mol/l) | | | | |
|---|---|---|---|---|---|
| | 0.5 day | 1 day | 4 days | 10 days | 20 days |
| 4 | 0.015 | 0.020 | 0.021 | 0.020 | 0.019 |
| Comparative Example 2 | 0.013 | 0.016 | 0.003 | — | — |

EXAMPLE 5

A continuous interesterification was carried out with employing the reaction liquid of 1 part by weight of olive oil, 1 part by weight of caprylic acid and 1 part by weight of hexane and the dried cells as those in Example 1, with adjusting the water concentration in the reaction liquid to 300 ppm in the same manner as in Example 1. The composition of the trigriceride in the reaction liquid was analyzed in the same manner as in Example 1, and the concentrations of product, 1,3-dicapryloyl-2-oleyl-glycerol (hereinafter referred to as "COC") in the reaction liquid determined 1, 4, 10 and 20 days after starting the interesterification and the values are shown in Table 3.

TABLE 3

| Example No. | Concentration of product COC in reaction liquid (mol/l) | | | |
|---|---|---|---|---|
| | 1 day | 4 days | 10 days | 20 days |
| 5 | 0.039 | 0.038 | 0.038 | 0.037 |

EXAMPLE 6

An interesterification was carried out continuously with employing the reaction liquid of 1 part by weight of middle melting fraction of palm oil, 1 part by weight of middle melting fraction of shea fat and 1 part by weight of hexane and dried cells which are the same as those in Example 1, and with adjusting the water concentration in the reaction liquid at 200 ppm, in the same manner as in Example 1. The composition of triglyceride was analyzed in the same manner as in Example 1, and the concentration of product 1-stearoyl-2-oleyl-3-palmitoyl-glycerol (hereinafter referred to as "SOP") in the reaction liquid were determined 1, 4, 10 and 20 days after the starting of the interesterification and the values are shown in Table 4.

TABLE 4

| Example No. | Concentration of product SOP in reaction liquid (mol/l) | | | |
|---|---|---|---|---|
| | 1 day | 4 days | 10 days | 20 days |
| 6 | 0.20 | 0.20 | 0.19 | 0.19 |

As in apparent from Table 3 and Table 4 of Example 5 and Example 6 respectively, the continuous interesterification could be carried out with adjusting the water concentration in the reaction liquid and the yields of the desired products in both Examples were maintained almost constantly for 20 days.

EXAMPLE 7

A continuous interesterification was carried out with employing a reacting apparatus shown in FIG. 5, dried cells having a water concentration of 4.0% by weight, which was obtained by further drying the dried cells used in Example 1 under reduced pressure for 12 hours, and the same reaction liquid as that in Example 1, and with circulating the reaction liquid so that the residence time in the reactor was 3 hours, and with adjusting the water concentration in the reaction liquid at 40 ppm. The reactor 1 and water dissolving unit 2 employed were the same as those in Example 1. The water removing unit 14 employed was a packed column of calcium chloride having an inner diameter of 2 cm and a height of 30 cm. The composition of triglyceride was analyzed in the same manner as in Example 1, and the concentrations of dried product SOS are shown in Table 5. On the other hand, the concentration of diglyceride in the reaction liquid was measured by means of column chromatography using tetrahydrofuran as eluent with a flow rate of 1 ml/min at a temperature of 30° C. with employing a series of four columns made by SHIMADZU CORPORATION (trade name: HGS 15 and HGS 20) to separate the reaction liquid into fractions of triglyceride, diglyceride, monoglyceride and fatty acid. The fractions were analyzed by means of a refractive index detector RI. The concentrations of diglyceride (hereinafter referred to as "DG") are shown also in Table 5.

EXAMPLE 8 AND COMPARATIVE EXAMPLE 4

In Example 8, a continuous interesterification was carried out employing the same dried cells and the same reaction liquid as those in Example 7, under the same conditions as those in Example 7, with adjusting the water concentration in the reaction liquid to 300 ppm.

In Comparative Example 3, the procedure of Example 8 was repeated except that the water concentration in the reaction liquid was not adjusted.

The results were analyzed in the same manner as in Example 7, and the results are shown in the Table 5.

As is apparent form Table 5, the productivity of the product in Example 7 in which the water concentration in the reaction liquid was adjusted to 40 ppm, was the highest compared with the productivities in Comparative Example 3 and Example 8. Further, the amount of formed DG in Example 7 was lower than that in Example 8, and it is understood that it was easy to remove the DG in refining the product SOS. Further, when the interesterification was carried out continuously without adding water as in Comparative Example 3, after some time, the reaction did not proceed any more. However, when the reaction was carried out with adding water to adjust the water concentration as in Examples 7 and 8, the desired products can be obtained at an almost constant concentration for 20 days.

TABLE 5

| Example No. | Concentration of product SOS in reaction liquid (mol/l) (Concentration of DG (mol/l)) | | | | |
|---|---|---|---|---|---|
| | 0.5 day | 1 day | 4 days | 10 days | 20 days |
| 7 | 0.040 (0.005) | 0.048 (0.005) | 0.049 (0.004) | 0.049 (0.003) | 0.048 (0.003) |
| 8 | 0.045 (0.009) | 0.046 (0.008) | 0.046 (0.009) | 0.044 (0.007) | 0.045 (0.006) |
| Comparative | | | | | |

TABLE 5-continued

| | Concentration of product SOS in reaction liquid (mol/l) (Concentration of DG (mol/l)) | | | | |
|---|---|---|---|---|---|
| | 0.5 day | 1 day | 4 days | 10 days | 20 days |
| Example 3 | 0.041 (0.003) | 0.045 (0.003) | 0.020 (0.002) | 0.003 (0.001) | — (—) |

EXAMPLE 9

A batch interesterification was carried out with employing 0.5 part by weight of the same dried cells as those in Example 1 and a reaction liquid of 1 part by weight of olive oil and 4 parts by weight of palmitoleic acid. In the interesterification, a reacting apparatus as shown in FIG. 7 was employed. The moisture adjusting unit 8 in the reacting apparatus shown in FIG. 7 was charged with an aqueous solution of glycerin which was prepared so that the water concentration in the reaction liquid was adjusted to 20 ppm.

After one hour, the reaction was stopped, and the cells were removed from the reaction liquid by filtration. The reaction liquid was analyzed in the same manner as in Example 1. The concentration of DG in the reaction liquid was analysed in the same manner as in Example 7. The concentrations of the product 1,3-dipalmitoleyl-2-oleyl-glycerol (hereinafter referred to as "P'OP'") and that of the by-product DG are shown in Table 6.

EXAMPLE 10, 11 AND 12

The same procedure as in Example 9 was repeated except that the aqueous solution of glycerin having different water concentration was charged to the moisture adjusting unit so that the water concentration in the reaction liquid was adjusted to 50 ppm (Example 10), 100 ppm (Example 11) or 250 ppm (Example 12). Thus the batch interesterification of Example 10, 11 and 12 were carried out. The reaction liquid was analyzed in the same manner as in Example 7. The results are shown in Table 6 together with the result of Example 9.

TABLE 6

| Example No. | 9 | 10 | 11 | 12 |
|---|---|---|---|---|
| Concentration of P'OP' (mol/l) | 0.050 | 0.063 | 0.060 | 0.055 |
| Concentration of DG (mol/l) | 0.002 | 0.004 | 0.007 | 0.013 |

From the results in Table 6, it was found that the smaller the adjusted water concentration in the reaction liquid was, the smaller the concentration of by-product DG was.

In addition to the ingredients used in the Examples, other ingredients can be used in the Examples as set forth in the specificaiton to obtain substantially the same result.

What we claim is:

1. A process of interesterification which comprises:
    subjecting a reaction liquid containing:
       (a) a fat or oil; and
       (b) a member selected from the group consisting of
          (i) a fat or oil differing from component (a)
          (ii) a fatty acid ester of a lower alcohol; and
          (iii) a fatty acid;
    to the action of a lipase contained in dry microbial cells or immobilized dry microbial cells said cells having a water content of 0.1 to 20% by weight, and belonging to Rhizopus species while adjusting water concentration by adding water to the reaction mixture so as to maintain a water concentration of the reaction mixture ranging from 30 to 300 ppm.

* * * * *